United States Patent [19]

Aoki

[11] Patent Number: 5,731,570
[45] Date of Patent: Mar. 24, 1998

[54] HEATER CONTROLLER FOR AN AIR-FUEL RATIO SENSOR

[75] Inventor: Keiichiro Aoki, Susono, Japan

[73] Assignee: Toyota Jidosha Kabushiki Kaisha, Toyota, Japan

[21] Appl. No.: 733,605

[22] Filed: Oct. 18, 1996

[30] Foreign Application Priority Data

Dec. 5, 1995 [JP] Japan ................................. 7-316592

[51] Int. Cl.[6] .................................................. H05B 1/02
[52] U.S. Cl. ........................... 219/497; 219/205; 219/207; 219/508; 123/697
[58] Field of Search ............................. 219/202–207, 219/497, 499, 501, 486, 505, 508, 509; 123/41.12, 41.15, 41.01, 689, 697, 23.32, 686; 307/117, 119

[56] References Cited

U.S. PATENT DOCUMENTS

| | | | |
|---|---|---|---|
| 5,144,916 | 9/1992 | Yoshida et al. | 123/41.12 |
| 5,353,775 | 10/1994 | Yamashita et al. | 123/686 |
| 5,544,640 | 8/1996 | Thomas et al. | 123/689 |

FOREIGN PATENT DOCUMENTS

A1-158335   6/1989   Japan.

*Primary Examiner*—Mark H. Paschall
*Attorney, Agent, or Firm*—Oliff & Berridge, PLC

[57] ABSTRACT

A heater control system for an air-fuel ratio sensor is shown to prevent the sensor from being cooled during an extended idling operation after high-load running. An oxygen concentration detecting element of an air-fuel ratio sensor is heated by a heater installed in the sensor, and its temperature is controlled to about 650° C. When a radiator cooling fan functions during idling or low-speed running after high-load running, a controller detects the functioning of the fan and increases an electric power supplied to the heater. A heater resistance detector detects a resistance of the heater. A storage device stores the detected heater resistance when it is determined that a temperature of the heater is stable based on an engine operating condition. Electric power supplied to the heater is increased in accordance with the difference between the detected resistance of the heater and the stored resistance. A heater controller thus prevents the air-fuel ratio sensor from being cooled by the fan to the point that detection accuracy of the sensor would deteriorate.

8 Claims, 9 Drawing Sheets

| ΔR | 0.5 | 1.0 | 1.5 |
|---|---|---|---|
| Pfan | 2 | 4 | 6 |

HEATER CONTROLLER FOR AN AIR-FUEL RATIO SENSOR

BACKGROUND OF THE INVENTION

1. Field of the Invention

This invention relates to a heater controller for an air-fuel ratio sensor, and especially relates to a heater controller for controlling an electric power supplied to a heater for heating an air-fuel ratio sensor to prevent the sensor being cooled during a long idling time after high-load running.

2. Description of the Related Art

It is widely known to control an air-fuel ratio of air-fuel mixture supplied into a cylinder of an engine at a fixed target air-fuel ratio (for example, a stoichiometric air-fuel ratio) by correcting a basic fuel flow rate in accordance with oxygen contained in exhaust gas in order to improve an exhaust gas emission, a specific fuel consumption and vehicle drivability.

To achieve the above-mentioned air-fuel ratio control, it is indispensable to detect the oxygen contained in the exhaust gas. It is also necessary to keep the temperature of an air-fuel ratio sensor at a fixed temperature (for example, 650° C.) by heating the sensor with a heater, because an output voltage of the sensor is influenced not only by the oxygen concentration but also by the temperature of the sensor.

However, as the temperature of the sensor is influenced by the temperature of exhaust gas, a heater controller which controls the electric power supplied to the heater according to the operating condition of the engine which influences the temperature of exhaust gas has been proposed (see Japanese Unexamined Patent Publication 1-158335).

Further, the above-mentioned heater controller also decreases the electric power based on the operating condition of the engine to prevent the sensor being overheated during a long idling time after high-load driving, because the temperature of exhaust gas becomes very high in this state.

However, the air-fuel ratio sensor is often mounted in the neighborhood of a radiator cooling fan. In this case, it is impossible to prevent the sensor being cooled by the fan and its temperature being decreased, because it functions during idling after high-load running (for example, when an automobile is parked with the engine is running after operating on an expressway).

SUMMARY OF THE INVENTION

Accordingly, an object of this invention is to provide a heater controller for an air-fuel ratio sensor able to prevent the sensor being cooled during a long idling time after high-load running.

According to one aspect of this invention, there is provided a heater controller, for controlling an electric power supplied to a heater in order to heat an air-fuel ratio sensor which detects an air-fuel ratio of an internal combustion engine, comprising a fan condition determining means for determining whether or not a radiator cooling fan is operating; an engine condition detecting means for detecting an operating condition of the engine; a base electric power determining means for determining a base electrical power supplied to a heater for heating the air-fuel ratio sensor in accordance with the engine operating condition detected by said engine condition detecting means; an auxiliary electric power determining means for determining an auxiliary electric power when it is determined that the radiator cooling fan is functioned by said fan condition determining means during idling or low speed running; and a power supply means for supplying an electric power which is a sum of the base electrical power determined by said base electric power determining means and the auxiliary electric power determined by said auxiliary electric power determining means.

As described above, the heater controller can prevent the temperature of the air-fuel ratio sensor decreasing, because the electric power supplied to the heater for heating the air-fuel ratio sensor is increased when the radiator cooling fan is operating during idling or low speed running.

According to another aspect of this invention, there is provided a heater controller for controlling an electric power supplied to a heater in order to heat an air-fuel ratio sensor which detect an air-fuel ratio of an internal combustion engine, comprising an engine condition detecting means for detecting an operating condition of the engine; a heater resistance detecting means for detecting a resistance of the heater; a storing means for storing the resistance of the heater detected by said heater resistance detecting means as a stored resistance when it is determined that the temperature of the heater has become stable based on the internal combustion engine operating condition detected by said engine condition detecting means; a base electric power determining means for determining a base electrical power supplied to the heater for heating the air-fuel ratio sensor in accordance with the internal combustion engine operating condition detected by said engine condition detecting means; an auxiliary electric power determining means for determining an auxiliary electric power in accordance with the resistance of the heater detected by said heater resistance detecting means and the stored resistance stored in said storing means during an idling or a low speed running; and a power supplying means for supplying an electric power which is a sum of the base electrical power determined by said base electric power determining means and the auxiliary electric power determined by said auxiliary electric power determining means.

As described above, the heater controller can more surely prevent decreasing the temperature of the air-fuel ratio sensor, because the electric power supplied to the heater for heating the air-fuel ratio sensor is increased in accordance with the stored resistance and the resistance of the heater when the radiator cooling fan is operating during an idling state or low speed running state.

BRIEF DESCRIPTION OF THE DRAWINGS

The present invention will be more clearly understood from the description set forth below with reference to the accompanying drawings; where.

DETAILED DESCRIPTION OF THE PREFERRED EMBODIMENT

Figure 1:
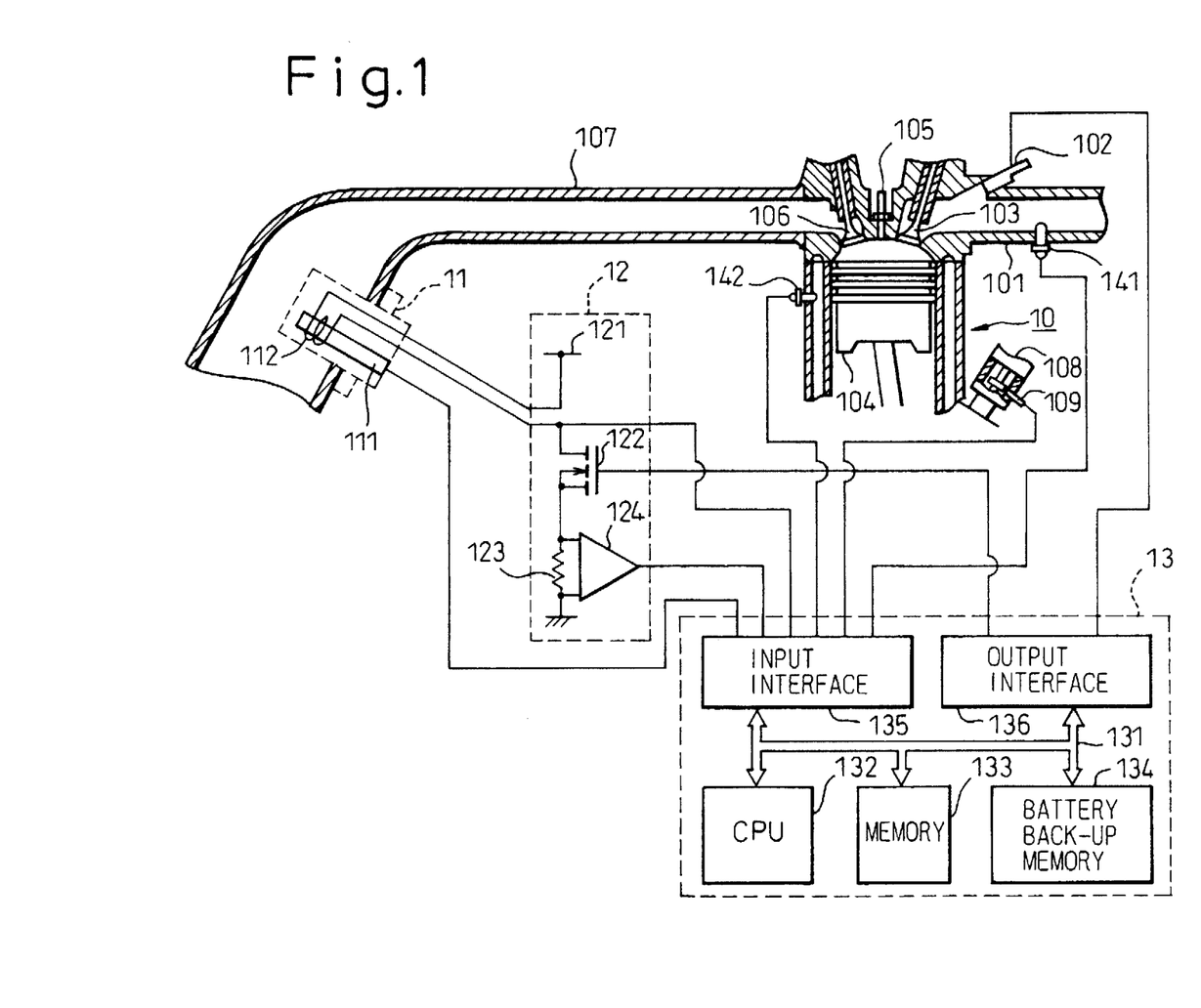
FIG. 1 is a block diagram of the preferred embodiment according to this invention.

FIG. 1 shows a diagram of the preferred embodiment of a heater controller for an air-fuel ratio sensor according to the present invention, wherein a mixture composed of air supplied through an intake pipe 101 and fuel injected from an injector 102 is supplied to an internal combustion engine 10 through an intake valve 103.

The mixture is compressed by a piston 104, and the compressed mixture is ignited by an igniter 105 then the piston 104 is pushed down. Exhaust gas produced by the burning of the mixture is exhausted to an exhaust pipe 107 through an exhaust valve 106.

The engine speed of the engine 10 is detected by a speed detector 109 built in a distributor 108.

On the exhaust pipe 107, an air-fuel ratio sensor 11 is installed. The air-fuel ratio sensor 11 has a detecting element 111 which detects oxygen concentration and a heater 112 which heats the detecting element 111.

The heater obtains an electric power from a driving circuit 12 which is composed of an electric power source 121, a switching element 122, a resistor 123 for measuring current, and a buffer amplifier 124.

The heater 112, the switching element 122, and the resistor 123 are connected in series between the electric power source 121 and an earth (the vehicle body). A current flowing through this series connection is detected by measuring a voltage across the resistor 123 for measuring a current through the buffer amplifier 124.

A controller 13 is a microcomputer system which is composed of a bus 131, CPU 132, a memory 133, a battery-backup memory 134, an input interface 135, and an output interface 136.

Note, data stored in the battery-backup memory 134 is not lost when a main switch of the automobile is turned off and further an ignition key is drawn out, as long as the battery-backup memory 134 is not removed from a battery (that is, as long as the memory is not cleared by removing the backup battery).

Not only the speed detector 109 and the detecting element 111 of the air-fuel ratio sensor 11, but also a vacuum sensor 141 installed on the intake pipe 101 and a coolant temperature sensor 142 are connected to the input interface 135.

A valve opening command for the injector 102 and an ON/OFF command for the switching element 122 are output from the output interface 136.

Figure 2:
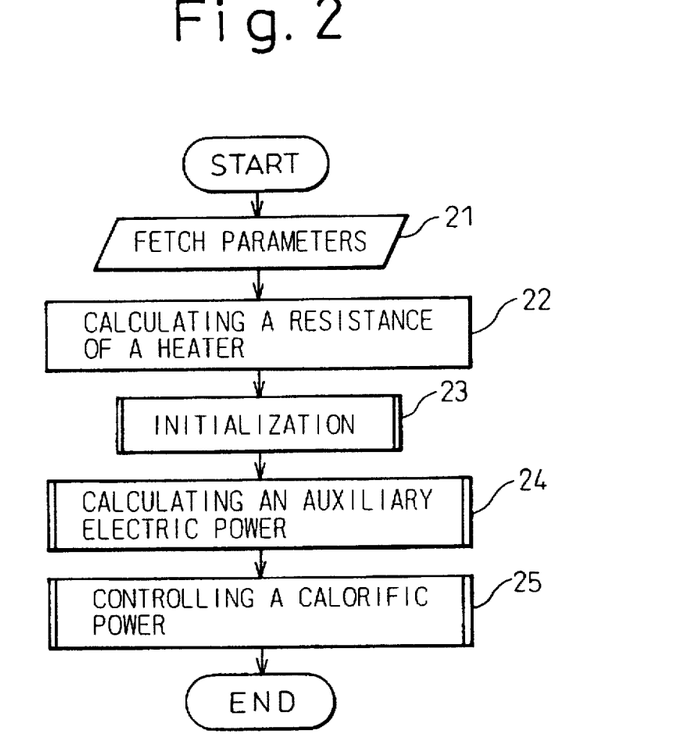
FIG. 2 is a flow chart of a heater control routine.

FIG. 2 shows a flow chart of a heater control routine executed in the controller 13. An engine speed Ne, a vacuum pressure Pm, a coolant temperature THw, a voltage Vh supplied to the heater, and a current Ih flowing through the heater are fetched at step 21.

At step 22, a resistance Rh of the heater is calculated based on the voltage Vh supplied to the heater and a current Ih flowing through the heater by using following equation.

$$Rh \leftarrow Vh/Ih$$

This routine is terminated after an initializing routine, an auxiliary electric power determining routine, and a calorific power determining routine are respectively executed at step 23, at step 24, and at step 25.

Figure 3:
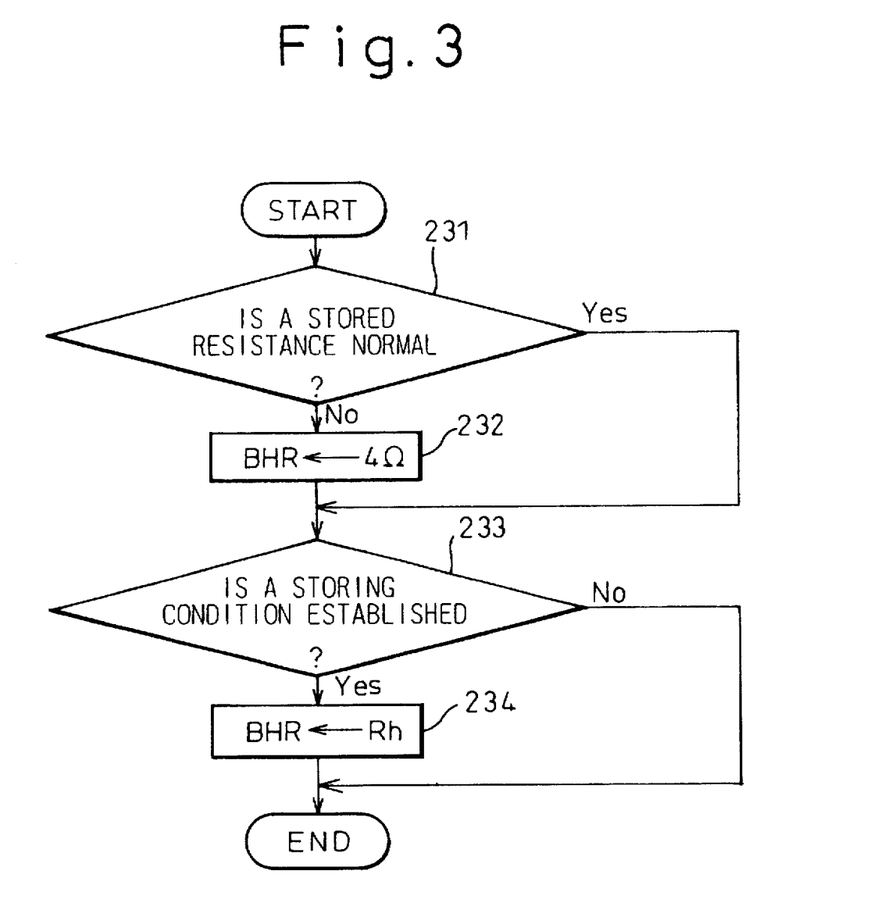
FIG. 3 is a flow chart of an initializing routine.

FIG. 3 shows a detailed flow chart of the initializing routine executed at step 23 of the heater control routine, and it is determined that whether or not a stored resistance of the heater stored in the battery backup memory 134 is normal at step 231.

The above-mentioned determination, for example, can be realized by storing not only the resistance of the heater but also its reciprocal at a storing step and confirming that those two numbers are mutually in a reciprocal relationship when determining whether or not the stored resistance is normal.

When the determination at step 231 is negative, the control proceeds to step 233 after the stored resistance BHR is set up to the predetermined standard value (for example, 4 ohms) at step 232. Note, when the determination at step 231 is affirmative, the control proceeds directly to step 233.

At step 233, it is determined whether or not a condition for storing a resistance of the heater is established.

The storing condition is established when the temperature of the heater is maintained at a fixed temperature and the operating condition of the automobile is stable. This condition can be confirmed by determining whether or not following three conditions are established.

(1) Whether or not an air-fuel ratio feedback control is being executed.

(2) Whether or not a state that the intake pressure Pm is below a predetermined fixed pressure and the engine speed Ne is below a predetermined fixed speed continues for a fixed predetermined interval.

(3) Whether or not the electric power supplied to the heater is above a predetermined fixed electric power.

When the determination at step 233 is affirmative, that is, when the storing condition is established, this routine is terminated after the stored resistance BHR is replaced with Rh which is calculated at step 22 of the heater control routine at step 234.

Note, when the determination at step 233 is negative, this routine is directly terminated without replacing of the stored resistance BHR.

Figure 4:
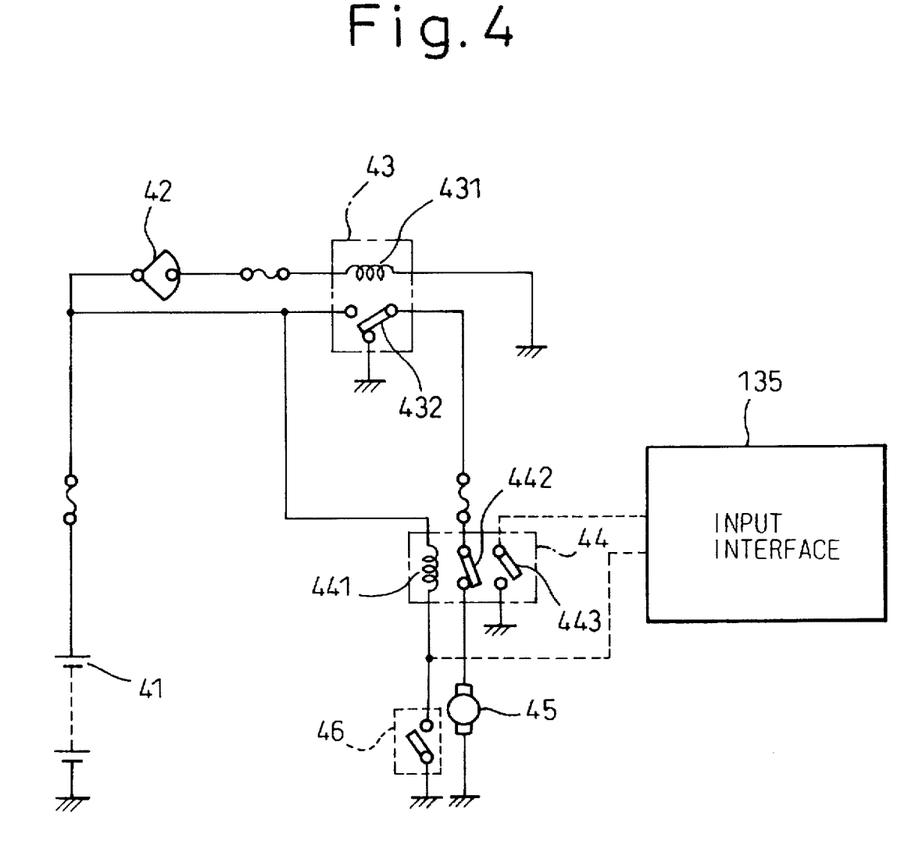
FIG. 4 is a circuit diagram of an electric power supply system.

FIG. 4 shows a circuit diagram of an electrical system in the automobile, and a negative pole of the battery 41 is connected to the body. A positive pole is connected to a coil 431 of a main relay 43 through an ignition switch 42.

When the ignition switch 42 is turned on, the coil 431 of the main relay 43 is energized, the contact 432 of the main relay 43 is closed, and the electrical power is supplied to a motor 45 for driving a radiator cooling fan through a contact 442 of a radiator cooling fan relay 44.

The positive pole of the battery 41 is also connected to a coolant temperature switch 46 through a coil 441 of the radiator cooling fan relay 44.

When the temperature of the coolant goes up to a predetermined fixed temperature, for example, 90° C., the coolant temperature switch 46 turns on and it makes the coil 441 of the radiator cooling fan relay 44 energized. Therefore, when a contact 442 of the radiator fan relay 44 is closed, the motor 45 begins to rotate and the radiator is cooled by the fan directly connected to the motor.

When the temperature of the coolant goes down to a predetermined fixed temperature, for example, 83° C., the coolant temperature switch 46 turns off and it makes the coil 441 of the radiator cooling fan relay 44 deenergized. Therefore, the contact of the radiator fan relay 44 is opened and the motor 45 of the radiator cooling fan is stopped.

Accordingly, the controller 13 can detect a condition of the radiator cooling fan by detecting an on/off state of an auxiliary contact 443 of the radiator cooling fan relay 44 or by detecting a voltage at a terminal of the coolant temperature switch 46 connected to the radiator cooling fan relay 44 to CPU 132 through the input-interface 135.

Figure 5:
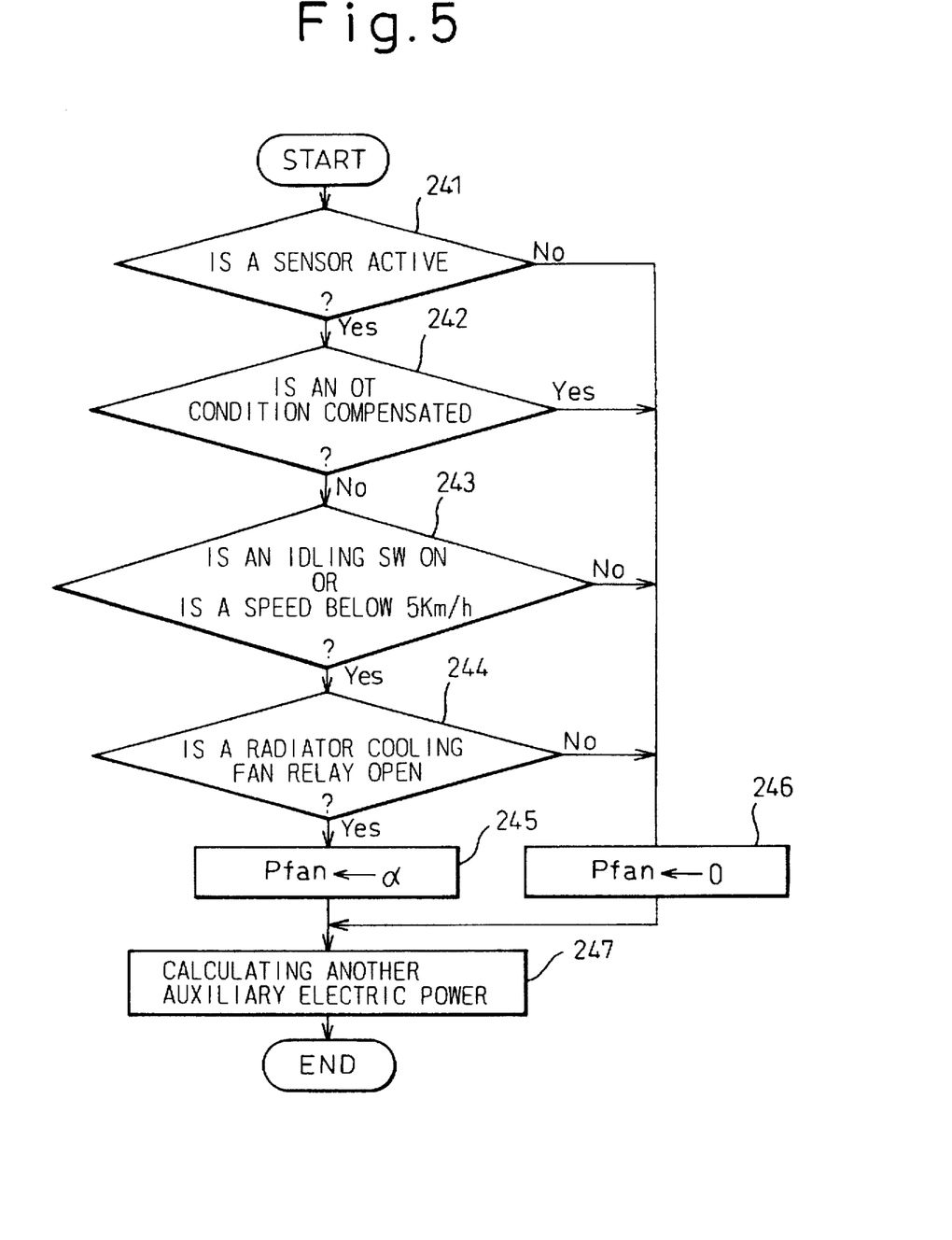
FIG. 5 is a flow chart of a first auxiliary electric power calculating routine.

FIG. 5 shows a first auxiliary electric power calculating routine, executed at step 24 of the heater control routine, which determines whether or not the air-fuel ratio sensor 11 is active. For example, the activity of the air-fuel ratio sensor 11 can be confirmed by determining whether or not an output of the air-fuel ratio sensor 11 goes above a predetermined fixed level in fuel cut condition.

When the determination at step 241 is affirmative, that is, when the air-fuel ratio sensor 11 is active, the control proceeds to step 242 where it is determined whether or not a condition for compensating for an over-temperature state (hereinafter, OT condition) is established. This is because an increase in an electric power becomes meaningless as the electric power is decreased when the OT condition is established.

When the determination at step 242 is negative, that is, when the OT condition is not established, the control proceeds to step 243 where it is determined whether or not an idling switch (not shown) is in an on-state or the automobile is running below a predetermined fixed low speed (for example, 5 Km/h).

When the determination at step 243 is affirmative, that is, when the automobile is idling in parked state or running below the predetermined fixed low speed, the control proceeds to step 244 where it is determined whether or not the auxiliary contact 443 of the radiator cooling fan relay 44 is closed.

Note, the determination at step 244 may confirm whether or not the voltage at the terminal of the coolant temperature switch 46 connected to the radiator cooling fan relay 44 is 0 volt.

When the determination at step 244 is affirmative, that is, when it is determined that the radiator cooling fan is functioning, the control proceeds to step 247 after an auxiliary electric power Pfan for compensating for the radiator cooling fan functioning state is set to a predetermined fixed positive value α at step 244.

When the determination at step 241 is negative, when the determination at step 242 is affirmative, and when the determination at step 244 is negative, the control proceeds step 247 after the auxiliary electric power Pfan for compensating the radiator cooling fan functioning state is set as "0" at step 247.

Another auxiliary electric power Poth (for example, an auxiliary electric power for compensating for a start-up condition to prevent the detecting element being cooled or an auxiliary electric power for compensating for a fuel-cut condition) is calculated at step 247 and this routine is terminated.

Figure 6:
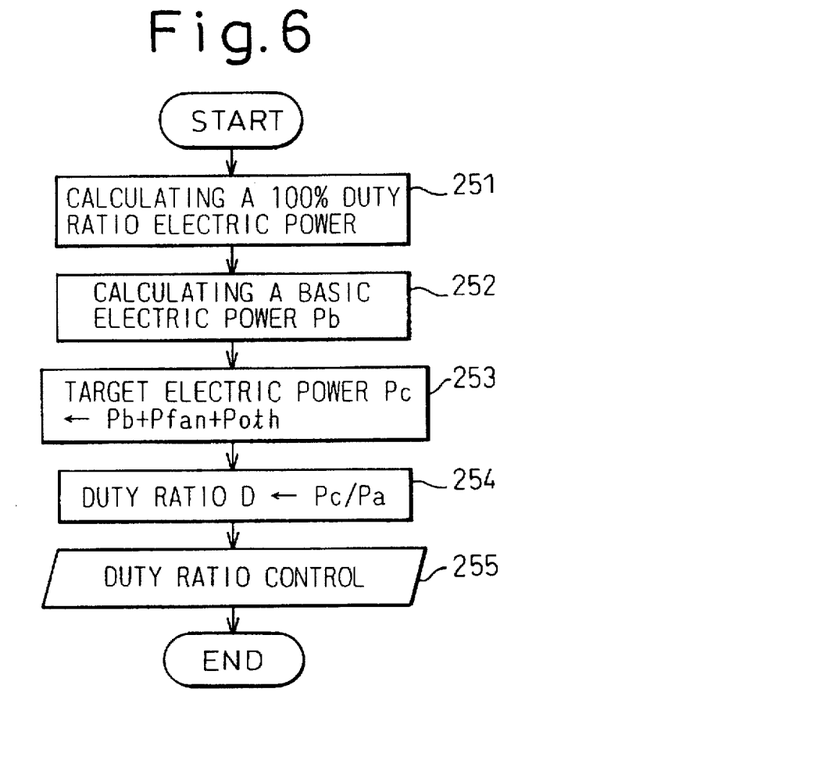
FIG. 6 is a flow chart of a calorific power control routine.

FIG. 6 shows a calorific power controlling routine executed the step 25 of the heater control routine, and an electric power Pa continuously supplied to the heater for a predetermined fixed period (for example, 100 ms), that is, an electric power at 100% duty ratio, is calculated based on the voltage supplied to the heater Vh and the current Ih flowing through the heater are fetched at step 21.

A basic electric power Pb required to maintain the temperature of the detecting element 111 at a predetermined fixed temperature under a current engine operating condition is calculated as a function of the engine speed Ne and the vacuum pressure Pm.

$$Pb \leftarrow Pb(Ne, Pm)$$

Figure 7:
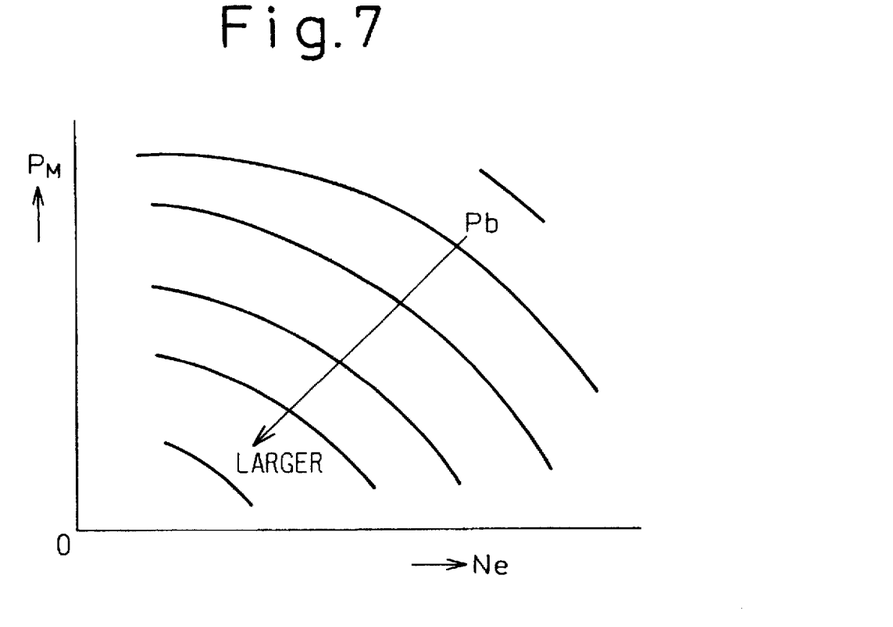
FIG. 7 is a graph to determine a basic electric power.

FIG. 7 shows a graph to determine the basic electric power Pb, and the ordinate denotes the vacuum pressure Pm and the abscissa denotes the engine speed Ne. Note, the parameter is the basic electric power Pb which becomes larger as the vacuum pressure Pm and the engine speed Ne become smaller, that is, as a quantity of exhaust gas becomes less and its temperature becomes lower.

A target electric power Pc is calculated by adding all auxiliary electric powers to the basic electric power Pb.

$$Pc \leftarrow Pb + Pfan + Poth$$

A duty ratio D is calculated as a ratio of the target electrical power Pc to the electrical power Pa at 100% duty ratio at step 254.

$$D \leftarrow Pc/Pa$$

The switching element 122 is switched with the duty ratio D to control the target electric power Pc supplied to the heater 112.

In the above-mentioned embodiment, it is determined whether or not the radiator fan is functioning by detecting the state of the radiator cooling fan relay. However, the functioning of the radiator cooling fan may be determined by the coolant temperature which is detected by the coolant temperature sensor 142. Therefore, the coolant temperature is used for determining whether or not the radiator cooling fan is functioning in a second auxiliary electric power calculating routine.

Figure 8:
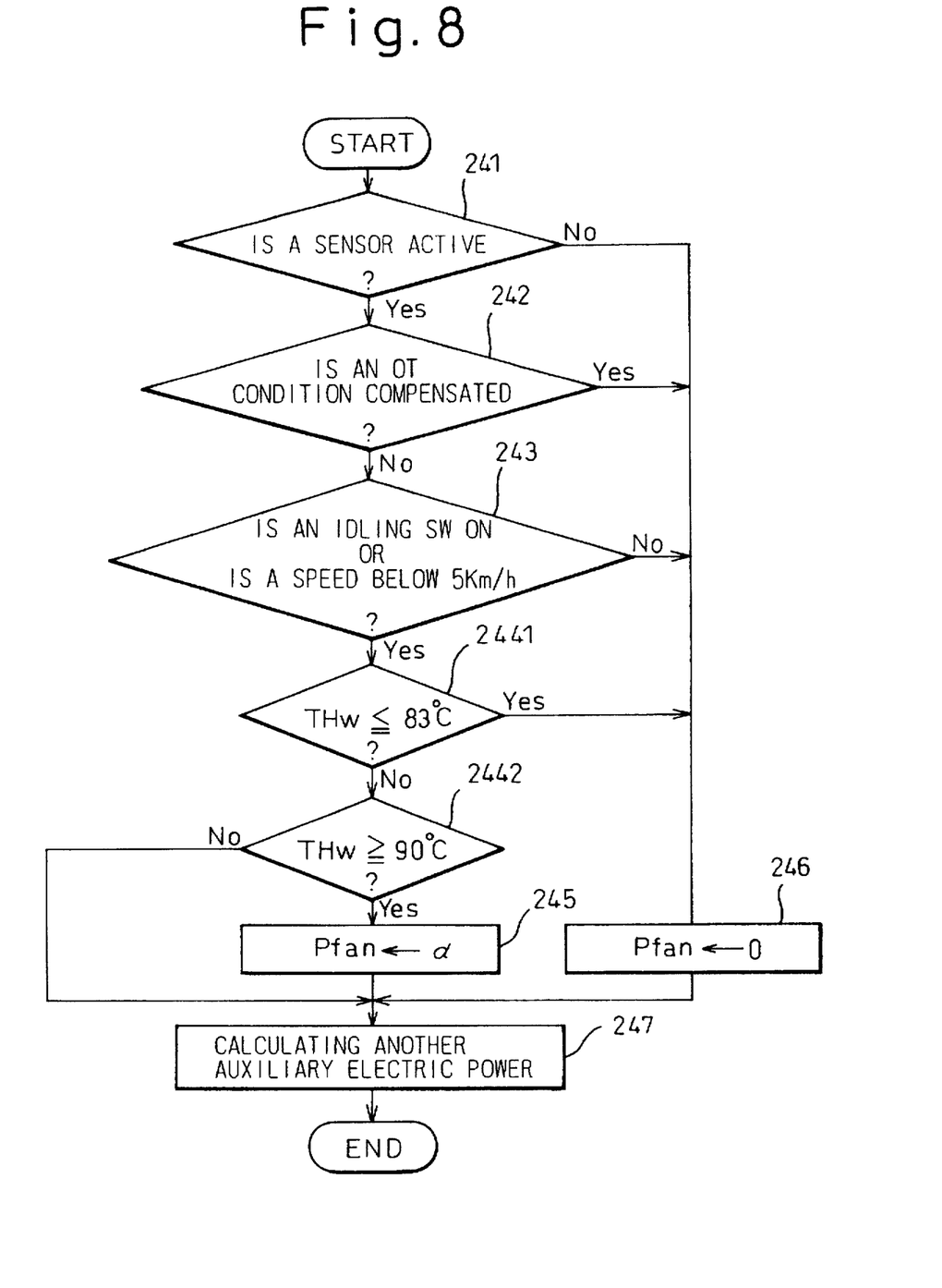
FIG. 8 is a flow chart of a second auxiliary electric power calculating routine.

FIG. 8 is a flow chart of a second auxiliary electric power calculating routine executed at step 24 of the heater control routine, and each step which has the same step number as in the first auxiliary electric power calculating routine executes the same process.

That is, it is determined whether or not the air-fuel ratio sensor 11 is active at step 241.

When the determination at step 241 is affirmative, that is, when the air-fuel ratio sensor 11 is active, the control proceeds to step 242 where it is determined whether or not the OT condition is established.

When the determination at step 242 is negative, that is, when the OT condition is not established, the control proceeds to step 243 where it is determined whether or not an idling switch (not shown) is in an on state or whether or not the automobile is running below a predetermined fixed low speed (for example, 5 Km/h).

When the determination at step 243 is affirmative, that is, when the automobile is idling in parked state or running below the predetermined fixed low speed, the control proceeds to step 2441 where it is determined whether or not the coolant temperature THw is below a low limit temperature (for example, 83° C.).

When the determination at step 2441 is negative, that is, when the coolant temperature THw is below the lower limit temperature, the control proceeds to step 2442 where it is determined whether or not the coolant temperature THw is over a upper limit temperature (for example, 90° C.).

When the determination at step 2442 is affirmative, that is, when the coolant temperature THw is over the upper limit temperature, the control proceeds to step 245.

At step 245, an auxiliary electric power Pfan for compensating for a radiator cooling fan functioning state is set as a predetermined fixed positive value α.

On the other hand, if the determination at step 2442 is negative, that is, when the coolant temperature THw is between the lower limit temperature and the upper limit temperature, the control proceeds to step 247 to maintain the previous state.

When the determination at step 241 is negative, when the determination at step 242 is affirmative, or when the determination at step 2441 is affirmative, the control proceeds to step 247 after the auxiliary electric power Pfan is set to zero at step 247.

Another auxiliary electric power Poth is calculated at step 247 and this routine is terminated.

Because the auxiliary electric power Pfan is determined as a fixed positive value while the radiator cooling fan is functioning in the first and second auxiliary electric power calculating routine, the auxiliary electric power Pfan may be insufficient in the case when the air-fuel ratio sensor 11 is cooled strongly.

Figure 9:
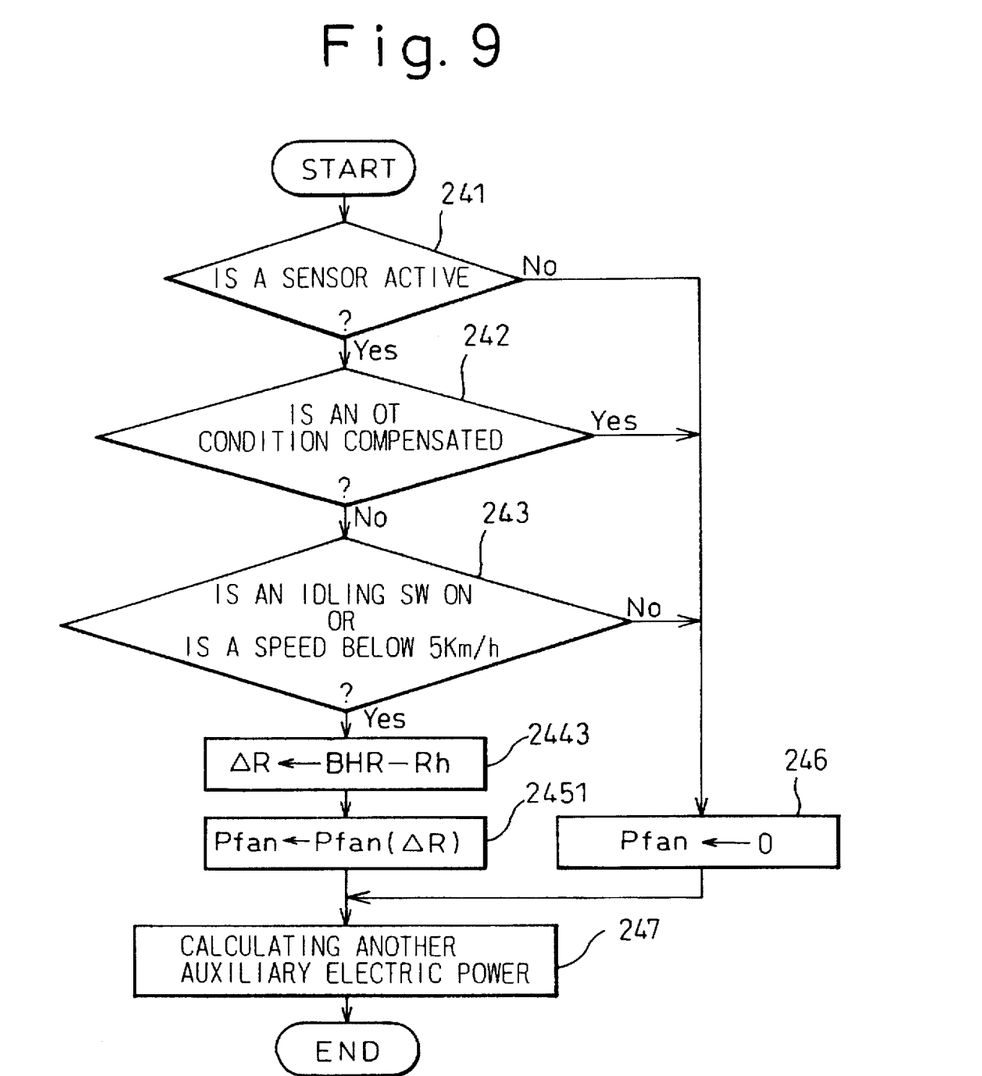
FIG. 9 is a flow chart of a third auxiliary electric power calculating routine.

The third auxiliary electric power calculating routine resolves the above-mentioned problem by changing the auxiliary electric power in accordance with the resistance of the heater.

FIG. 9 shows the third auxiliary electric power calculating routine executed at step 24 of the heater control routine, and each step having same step number as in the first collecting electric power calculating process executes the same process.

That is, it is determined whether or not the air-fuel ratio sensor 11 is active at step 241.

When the determination at step 241 is affirmative, that is, when the air-fuel ratio sensor 11 is active, the control proceeds to step 242 where it is determined whether or not the OT condition is established.

When the determination at step 242 is negative, that is, when the OT condition is not established, the control proceeds to step 243 where it is determined whether or not an idling switch (not shown) is in on state or whether or not the automobile is running below a predetermined fixed low speed (for example, 5 Km/h).

When the determination at step 243 is affirmative, that is, when the automobile is idling in parked state or running below the predetermined fixed low speed, the control proceeds to step 2443 where a resistance difference ΔR between the stored resistance BHR and the current heater resistance Rh calculated at step 22 of the heater control routine is calculated.

At step 2451, the auxiliary electric power Pfan is determined as the function of the resistance difference ΔR, and the control proceeds to step 247.

Figure 10:
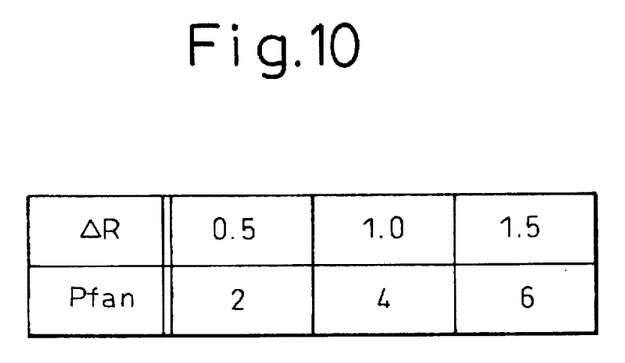
FIG. 10 is a map to determine a auxiliary electric power for compensating for the functioning of a radiator cooling fan.

FIG. 10 shows a map to determine the auxiliary electric power Pfan which is stored in the memory 133. The larger the resistance difference ΔR is, the larger the auxiliary electric power Pfan becomes.

When the determination at step 241 is negative, when the determination at step 242 is affirmative, or when the determination at step 243 is negative, the control proceeds to step 247 after the auxiliary electric power Pfan is set to zero at step 246.

Another auxiliary electric power Poth is calculated at step 247 and this routine is terminated.

Therefore, it is possible to surely prevent the temperature of the air-fuel ratio sensor 11 decreasing, because the auxiliary electric power is varied in accordance with the temperature of the air-fuel ratio sensor 11.

I claim:

1. A heater controller for controlling an electric power supplied to a heater for heating an air-fuel ratio sensor which detects an air-fuel ratio of an internal combustion engine, comprising:

a fan condition determining means for determining whether or not a radiator cooling fan is functioning;

an engine condition detecting means for detecting an operating condition of the internal combustion engine;

a base electric power determining means for determining a base electric power supplied to the heater for heating the air-fuel ratio sensor in accordance with the internal combustion engine operating condition detected by said engine condition detecting means;

an auxiliary electric power determining means for determining an auxiliary electric power when it is determined that the radiator cooling fan is functioning by said fan condition determining means; and an electric power supply means for supplying an electric power which is a sum of the base electric power determined by said base electric power determining means and the auxiliary electric power determined by said auxiliary electric power determining means.

2. The heater controller of the claim 1, wherein said fan condition determining means is a means for detecting whether or not a contact of a radiator cooling fan relay closes.

3. The heater controller of the claim 1, wherein said fan condition determining means is a means for detecting whether or not a coolant temperature detected by a coolant temperature sensor is higher than a predetermined fixed temperature.

4. A heater controller for controlling an electric power supplied to a heater for heating an air-fuel ratio sensor which detects an air-fuel ratio of an internal combustion engine, comprising:

an engine condition detecting means for detecting an operating condition of the internal combustion engine;

a heater resistance detecting means for detecting a resistance of the heater;

a storing means for storing the resistance of the heater detected by said heater resistance detecting means as a stored resistance when it is determined that a temperature of the heater is stable based on the internal combustion engine operating condition detected by said engine condition detecting means;

a base electric power determining means for determining a base electric power supplied to a heater for heating the air-fuel ratio sensor in accordance with the internal combustion engine operating condition detected by said engine condition detecting means;

an auxiliary electric power determining means for determining an auxiliary electric power in accordance with the resistance of the heater detected by said heater resistance detecting means and stored resistance stored in said storing means during an idling or a low-speed running; and an electric power supplying means for supplying an electric power which is a sum of the base electric power determined by said base electric power determining means and the auxiliary electric power determined by said auxiliary electric power determining means.

5. A heater control method for controlling an electric power supplied to a heater for heating an air-fuel ratio sensor which detects an air-fuel ratio of an internal combustion engine, comprising the steps of:

determining whether or not a radiator cooling fan is functioning;

detecting an operating condition of the internal combustion engine;

determining a base electric power supplied to the heater for heating the air-fuel ratio sensor in accordance with the internal combustion engine operating condition detected at said engine condition detecting step;

determining an auxiliary electric power when it is determined that the radiator cooling fan is functioning at said fan condition determining step; and supplying an electric power which is a sum of the base electric power determined at said base electric power determining step and the auxiliary electric power determined at said auxiliary electric power determining step.

6. The heater control method of the claim 5, wherein said fan condition determining step is a step for detecting whether or not a contact of a radiator cooling fan relay is closed.

7. The heater control method of the claim 5, wherein said fan condition determining step is a step for detecting whether or not a coolant temperature detected by a coolant temperature sensor is higher than a predetermined fixed temperature.

8. A heater control method for controlling an electric power supplied to a heater for heating an air-fuel ratio sensor which detects an air-fuel ratio of an internal combustion engine, comprising steps of:

detecting an operating condition of the internal combustion engine;

detecting a resistance of the heater;

storing the resistance of the heater detected at said heater resistance detecting step as a stored resistance when it is determined that the temperature of the heater is stable based on the internal combustion engine operating condition detected at said engine condition detecting step;

determining a base electric power supplied to the heater for heating the air-fuel ratio sensor in accordance with the internal combustion engine operating condition detected at said engine condition detecting step;

determining an auxiliary electric power in accordance with the resistance of the heater detected at said heater resistance detecting step and the stored resistance stored at said storing step; and supplying an electric power which is a sum of the base electrical power determined at said base electric power determining step and the auxiliary electric power determined at said auxiliary electric power determining step.

* * * * *